(12) United States Patent
Huehn et al.

(10) Patent No.: US 11,864,992 B2
(45) Date of Patent: *Jan. 9, 2024

(54) BERNOULLI GRIPPER FOR INTRAOCULAR AND CONTACT LENSES

(71) Applicant: Alcon Inc., Fribourg (CH)

(72) Inventors: Dominik Huehn, Grosswallstadt (DE); Jochen Koehler, Aschaffenburg (DE)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/651,493

(22) Filed: Feb. 17, 2022

(65) Prior Publication Data

US 2022/0168095 A1 Jun. 2, 2022

Related U.S. Application Data (63) Continuation of application No. 16/174,429, filed on Oct. 30, 2018, now Pat. No. 11,284,994.

(60) Provisional application No. 62/579,971, filed on Nov. 1, 2017.

(51) Int. Cl.
*A61F 2/16* (2006.01)
*A61F 9/00* (2006.01)

(52) U.S. Cl.
CPC ............ *A61F 2/1664* (2013.01); *A61F 2/16* (2013.01); *A61F 9/0061* (2013.01); *A61F 2002/1681* (2013.01)

(58) Field of Classification Search
CPC .... A61F 2/1662; A61F 2/1664; A61F 2/1675; A61F 2/1691; A61F 2002/1681; A61F 2002/16903; A61F 9/0061
See application file for complete search history.

(56) References Cited

U.S. PATENT DOCUMENTS

| | | | |
|---|---|---|---|
| 3,466,079 A * | 9/1969 | Mammel | H01L 21/6838 294/64.3 |
| 3,897,968 A | 8/1975 | Allen, Jr. | |
| 4,029,351 A * | 6/1977 | Apgar | B66C 1/0231 271/97 |
| 4,184,292 A | 1/1980 | Defazio et al. | |
| 4,257,637 A * | 3/1981 | Hassan | B66C 1/0218 271/97 |

(Continued)

FOREIGN PATENT DOCUMENTS

| | | |
|---|---|---|
| CN | 1266174 A | 9/2000 |
| CN | 102713310 A | 10/2012 |
| DE | 1227216 B | 10/1966 |

(Continued)

*Primary Examiner* — Sarah W Aleman
(74) *Attorney, Agent, or Firm* — PATTERSON + SHERIDAN, LLP (57) ABSTRACT

A Bernoulli gripper for ophthalmic lenses includes a gripper body with a first cavity corresponding in shape to an optic zone of an ophthalmic lens and a first channel formed within the gripper body. The first channel penetrates the first cavity at one end and includes a first port in the gripper body at another end of the first channel. The first channel is enabled to supply a fluid medium from the first port to the first cavity at a first velocity such that the ophthalmic lens positioned with the optic zone in proximity to the first cavity is subject to a first pressure force against the first cavity by the Bernoulli effect.

17 Claims, 6 Drawing Sheets

(56) References Cited

U.S. PATENT DOCUMENTS 9,339,374 B2 * 5/2016 Cole .................. A61F 2/1691

FOREIGN PATENT DOCUMENTS

| EP | 3081349 | A1 | 10/2016 |
| GB | 748138 | A | 4/1956 |
| JP | 2003-103646 | A | 9/2001 |
| TW | 393423 | B | 6/2000 |
| WO | 02059163 | A1 | 8/2002 |
| WO | 2009041861 | A1 | 4/2009 |
| WO | 2010094343 | A1 | 8/2010 |
| WO | 2011027546 | A1 | 3/2011 |

* cited by examiner

BERNOULLI GRIPPER FOR INTRAOCULAR AND CONTACT LENSES

CROSS-REFERENCE TO RELATED APPLICATIONS

This application is a continuation of U.S. patent application Ser. No. 16/174,429, filed Oct. 30, 2018, which claims priority to and benefit of U.S. Provisional Patent Application No. 62/579,971, filed Nov. 1, 2017, the entire contents of each of which are incorporated by reference herein in their entirety.

FIELD

The present disclosure relates generally to manufacturing and handling of medical devices, and more specifically, to a Bernoulli gripper for intraocular and contact lenses.

BACKGROUND

The human eye includes a cornea and a crystalline lens that are intended to focus light that enters the pupil of the eye onto the retina. However, the eye may exhibit various refractive errors which result in light not being properly focused upon the retina, and which may reduce visual acuity. Ocular aberrations can range from the relatively simple spherical and cylindrical errors that cause myopia, hyperopia, or regular astigmatism, to more complex refractive errors that can cause, for example, halos and starbursts in a person's vision.

Many interventions have been developed over the years to correct various ocular aberrations. These include spectacles, contact lenses, corneal refractive surgery, such as laser-assisted in situ keratomileusis (LASIK) or corneal implants, and intraocular lenses (IOLs). The diagnosis and specification of sphero-cylindrical spectacles and contact lenses for treatment of myopia, hyperopia, and astigmatism are also well-established.

In particular, IOLs and contact lenses are small, delicate, and sensitive optical parts. The handling and transfer of IOLs and contact lenses, such as during manufacturing, may involve different operations, in which a contact lens or an IOL is physically manipulated. The materials used in IOLs and contact lenses may be highly sensitive to physical contact. During handling and transfer operations, any physical contact with a contact lens or an IOL may result in damage to the lens, and in particular to a surface of the lens, which is undesirable.

SUMMARY

In one aspect, a disclosed Bernoulli gripper is for gripping ophthalmic lenses, such as IOLs and contact lenses. The Bernoulli gripper may include a gripper body with a first cavity corresponding in shape to an optic zone of an ophthalmic lens, and a first channel formed within the gripper body, the first channel penetrating the first cavity at one end and comprising a first port in the gripper body at another end of the first channel. In the Bernoulli gripper, the first channel may be enabled to supply a fluid medium from the first port to the first cavity at a first velocity such that the ophthalmic lens positioned with the optic zone in proximity to the first cavity is subject to a first pressure force against the first cavity by the Bernoulli effect.

In any of the disclosed implementations of the Bernoulli gripper, the pressure force may be sufficient to grip the ophthalmic lens at the first cavity to enable positioning of the ophthalmic lens when the gripper body is correspondingly positioned.

In any of the disclosed implementations of the Bernoulli gripper, the first cavity may be enabled to grip the ophthalmic lens without the optic zone contacting the first cavity when the first pressure force acts against the first cavity.

In any of the disclosed implementations of the Bernoulli gripper, the first channel may be enabled to supply the fluid medium when the fluid medium is electrostatically charged.

In any of the disclosed implementations of the Bernoulli gripper, the fluid medium may be air.

In any of the disclosed implementations of the Bernoulli gripper, the ophthalmic lens may be an intraocular lens comprising the optic zone and a haptic, while the Bernoulli gripper further includes a mechanical stop to detain the haptic and prevent rotation of the ophthalmic lens. In the Bernoulli gripper, the mechanical stop may further include a second cavity correspondingly formed to receive a distal portion of the haptic, while the Bernoulli gripper further includes a second channel formed within the gripper body, the second channel penetrating the second cavity at one end and comprising a second port in the gripper body at another end of the second channel, the second port different from the first port. In the Bernoulli gripper, the second channel may be enabled to supply the fluid medium from the second port to the second cavity at a second velocity such that the haptic positioned in proximity to the second cavity is subject to a second pressure force against the second cavity by the Bernoulli effect. In the Bernoulli gripper, the mechanical stop may further include a first vacuum port for applying underpressure to the haptic when the haptic is detained by the mechanical stop, while the first vacuum port is at one end of a third channel formed in the gripper body, the third channel comprising a third port at another end of the third channel, the third port different from the first port.

In any of the disclosed implementations of the Bernoulli gripper, the first channel may penetrate the first cavity at a center portion of the first cavity, while the Bernoulli gripper may further include a fourth channel formed within the gripper body, the fourth channel penetrating an edge portion of the first cavity at one end and comprising a fourth port in the gripper body at another end of the fourth channel. In the Bernoulli gripper, the fourth channel may be enabled to supply the fluid medium from the fourth port to the edge portion of the first cavity at a third velocity such that the ophthalmic lens positioned with the optic zone in proximity to the first cavity is subject to a third pressure force laterally within the first cavity by the Bernoulli effect.

In any of the disclosed implementations of the Bernoulli gripper, the ophthalmic lens may be an intraocular lens comprising the optic zone and a haptic, while the Bernoulli gripper further includes a second vacuum port for applying underpressure to the haptic when the optic zone is detained in the first cavity. In the Bernoulli gripper, the second vacuum port may be one end of a fifth channel formed in the gripper body, the fifth channel comprising a fifth port at another end of the fifth channel, the fifth port different from the first port.

In another disclosed aspect, a method for gripping ophthalmic lenses is disclosed. The method may include placing a gripper body in proximity to an ophthalmic lens, the gripper body having a first cavity corresponding in shape to an optic zone of the ophthalmic lens and a first channel formed within the gripper body, the first channel penetrating the first cavity at one end and comprising a first port in the gripper body at another end of the first channel. The method may also include supplying a fluid medium from the first port through the first channel to the first cavity at a first velocity such that the ophthalmic lens positioned with the optic zone in proximity to the first cavity is subject to a first pressure force against the first cavity by the Bernoulli effect.

In any of the disclosed implementations of the method, the pressure force may be sufficient to grip the ophthalmic lens at the first cavity to enable positioning of the ophthalmic lens when the body is correspondingly positioned, while the method may further include positioning the gripper body by moving the gripper body, and discontinuing supplying the fluid medium to the first cavity, whereby the ophthalmic lens is released from the gripper body.

In any of the disclosed implementations of the method, supplying the fluid medium may further include gripping the ophthalmic lens without the optic zone contacting the first cavity when the first pressure force acts against the first cavity.

In any of the disclosed implementations of the method, supplying the fluid medium may further include supplying the fluid medium through the first channel when the fluid medium is electrostatically charged.

In any of the disclosed implementations of the method, the fluid medium may be air.

In any of the disclosed implementations of the method, the ophthalmic lens may be an intraocular lens comprising the optic zone and a haptic, while the method may further include detaining the haptic using a mechanical stop formed within the gripper body to prevent rotation of the ophthalmic lens.

In any of the disclosed implementations of the method, the mechanical stop may further include a second cavity correspondingly formed to receive a distal portion of the haptic, while the method may further include placing the distal portion of the haptic in proximity to the second cavity, the second cavity comprising a second channel formed within the gripper body, the second channel penetrating the second cavity at one end and comprising a second port in the gripper body at another end of the second channel, the second port different from the first port. The method may also include supplying the fluid medium from the second port through the second channel to the second cavity at a second velocity such that the distal portion of the haptic positioned in proximity to the second cavity is subject to a second pressure force against the second cavity by the Bernoulli effect. The method may further include applying underpressure from a first vacuum port included with the mechanical stop to the haptic when the haptic is detained by the mechanical stop, while the first vacuum port is at one end of a third channel formed in the body, the third channel comprising a third port at another end of the third channel, the third port different from the first port.

In any of the disclosed implementations of the method, the first channel may penetrate the first cavity at a center portion of the first cavity, while the method may further include placing the optic zone in proximity to a fourth channel formed within the body, the fourth channel penetrating an edge portion of the first cavity at one end and comprising a fourth port in the body at another end of the fourth channel, and supplying the fluid medium through the fourth channel from the fourth port to the edge portion of the first cavity at a third velocity such that the ophthalmic lens positioned with the optic zone in proximity to the first cavity and the fourth channel is subject to a third pressure force laterally within the first cavity by the Bernoulli effect.

In any of the disclosed implementations of the method, the ophthalmic lens may be an intraocular lens comprising the optic zone and a haptic, while the method may further include applying underpressure at a second vacuum port to the haptic when the optic zone is detained in the first cavity, wherein the second vacuum port is one end of a fifth channel formed in the body, the fifth channel comprising a fifth port at another end of the fifth channel, the fifth port different from the first port.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

Throughout this disclosure, a hyphenated form of a reference numeral refers to a specific instance of an element and the un-hyphenated form of the reference numeral refers to the element generically or collectively. Thus, as an example (not shown in the drawings), device "12-1" refers to an instance of a device class, which may be referred to collectively as devices "12" and any one of which may be referred to generically as a device "12". In the figures and the description, like numerals are intended to represent like elements.

As noted above, ophthalmic lenses, such as IOLs and contact lenses, are small delicate parts that may present certain challenges in handling and manipulation, such as during manufacture, testing, and packaging, among other operations. For example, ophthalmic lenses, such as IOLs and contact lenses, may have optic zones that are as small as about 6 mm wide and may have a mass less than about 30 mg. In particular, the handling, manipulation, transfer, or other processing operations that are performed using physical contact with the ophthalmic lens and certain manufacturing equipment, such as holders or grippers, may be disadvantageous. For example, certain IOLs may be sticky on the surface and, therefore, sensitive to contact during certain manufacturing steps. In another example, certain operations, such as extraction, coating, or washing, may not be properly performed when a portion of the ophthalmic lens is in contact with manufacturing equipment and is not freely exposed or partially covered. Furthermore, certain manufacturing operations, such as drying of ophthalmic lenses after extraction, or releasing an ophthalmic lens that has been statically charged, may be adversely affected by contact of the lens to the manufacturing equipment, and may result in undesirable damage to the lens.

As will be described in further detail herein, a Bernoulli gripper for IOLs and contact lenses is disclosed. The Bernoulli gripper for IOLs and contact lenses disclosed herein is enabled to grip the lens in a contact-free manner. The Bernoulli gripper for IOLs and contact lenses disclosed herein may be used for holding, transporting, and releasing sticky and otherwise sensitive lenses, such as during various manufacturing operations. The Bernoulli gripper for IOLs and contact lenses disclosed herein may prevent damage to the lens during handling, positioning, or other manufacturing operations, such as coating and drying, for example. The Bernoulli gripper for IOLs and contact lenses disclosed herein may be used to isolate and detain the lens, in order to align or precisely position the lens, including rotational, lateral, azimuthal, and axial alignment.

The Bernoulli gripper for IOLs and contact lenses disclosed herein may be used during extraction or coating operations in order to keep desired surfaces of the lens exposed to facilitate an improvement of the particular operation being performed. The Bernoulli gripper for IOLs and contact lenses disclosed herein may avoid damage to the lens during manufacture, such as surface defects that may occur due to adhesion to a gripper or a carrier. The Bernoulli gripper for IOLs and contact lenses disclosed herein may be used in drying operations for a lens, where an extraction medium is evaporated from the surface of the lens and the lens may shrink and adhere to a surface of the gripper or carrier, which is avoided by the contact-free operation of the Bernoulli gripper. The Bernoulli gripper for IOLs and contact lenses disclosed herein may be used to improve the homogeneity of the drying operation for a lens, by keeping the lens surfaces exposed. The Bernoulli gripper for IOLs and contact lenses disclosed herein may be used to discharge or neutralize electrostatically charged lenses, which may be difficult to release from the gripper or carrier, because of the electrostatic attractive forces. The Bernoulli gripper for IOLs and contact lenses disclosed herein may be used with a fluid medium that includes ionized air for neutralizing any electrostatic charges on the lens.

Figure 1:
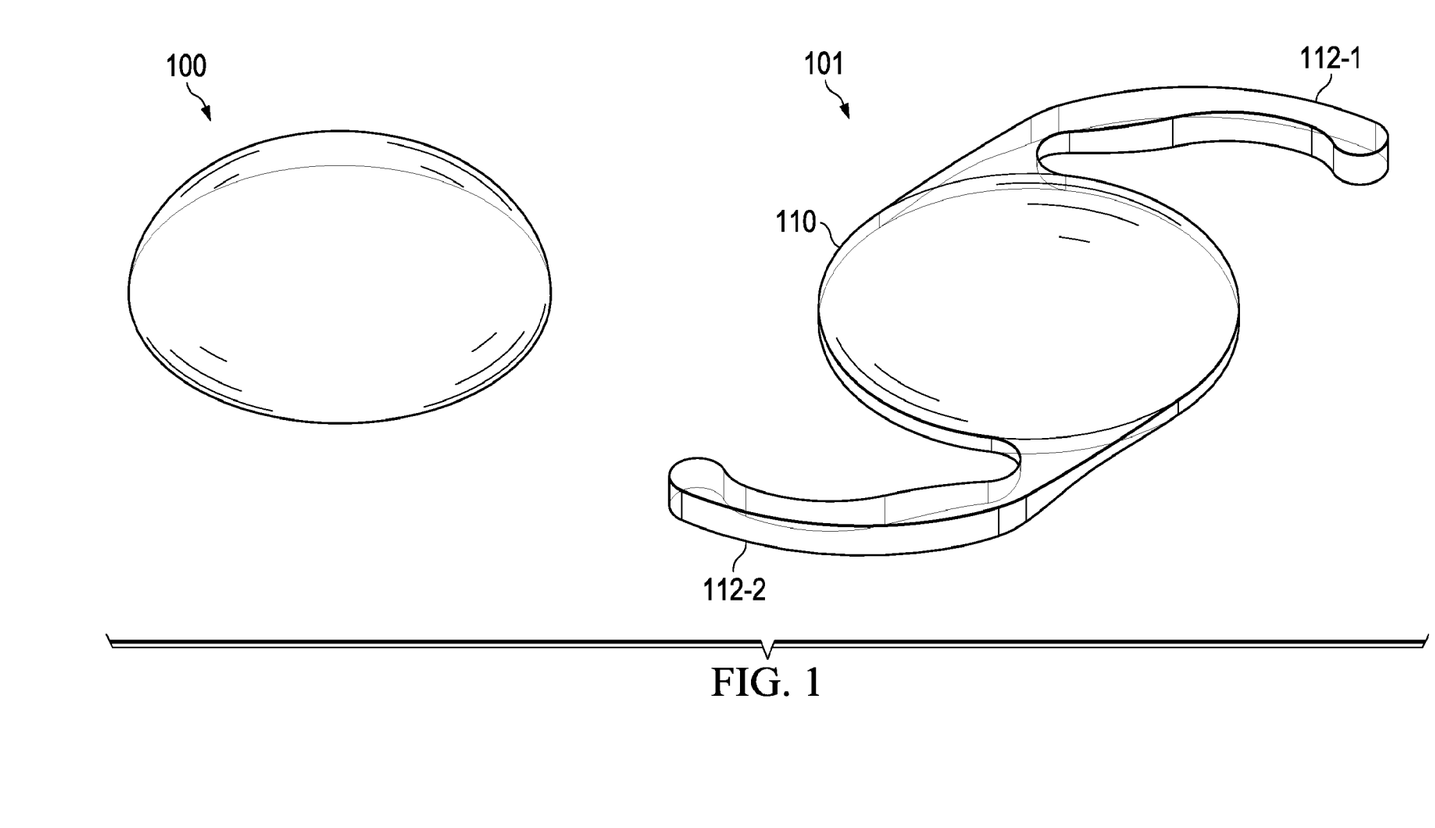
FIG. 1 is a depiction of a contact lens and an IOL.

Referring now to the drawings, FIG. 1 illustrates an exemplary depiction of a contact lens 100 and an IOL 101. FIG. 1 is a schematic diagram for descriptive purposes and is not drawn to scale or perspective.

In FIG. 1, contact lens 100 may represent any kind of contact lenses used for vision correction. For example, contact lens 100 may be a soft contact lens, such as a hydrogel lens or a silicone hydrogel lens, among others. Contact lens 100 may be a rigid gas permeable lens, such as a silicone acrylate lens or a fluoro-silicone acrylate lens, among others. In some instances, contact lens 100 may be a hybrid lens, such as with a central rigid gas permeable optical zone and an outer peripheral zone that is formed from a soft contact lens material. A diameter of contact lens 100 may be selected to correspond to a biometric dimension of the patient, such as a corneal diameter. In some implementations, contact lens 100 may be produced using a double-sided molding (DSM) process. Contact lens 100 may have a particular shape and thickness to achieve a desired optical performance. An outer surface shape or contour of contact lens 100 may enable contact lens 100 to be used with the Bernoulli grippers described herein.

Also in FIG. 1, IOL 101 may represent any kind of IOL used in ophthalmology. As shown, IOL 101 includes an optic zone 110 and two haptics 112-1, 112-2, which are shown in an exemplary configuration for descriptive purposes. In various implementations, IOL 101 may include different types and numbers of haptics 112. The materials used for optic zone 110 and haptics 112 may vary. For example, IOL 101 may be a non-foldable rigid IOL, such as with optic zone 110 comprising a polymethyl methacrylate (PMMA) lens. In some implementations, IOL 101 may be a flexible IOL, in which optic zone 110 may be comprised of various materials, such as silicone, hydrophobic acrylic, hydrophilic acrylic, hydrogel, collamer or combinations thereof. In IOL 101, haptics 112 may also be comprised of various materials, such as polypropylene, PMMA, hydrophobic acrylic, hydrophilic acrylic, silicone or combinations thereof. An outer surface shape or contour of IOL 101 may enable IOL 101 to be used with the Bernoulli grippers described herein.

Figure 2A:
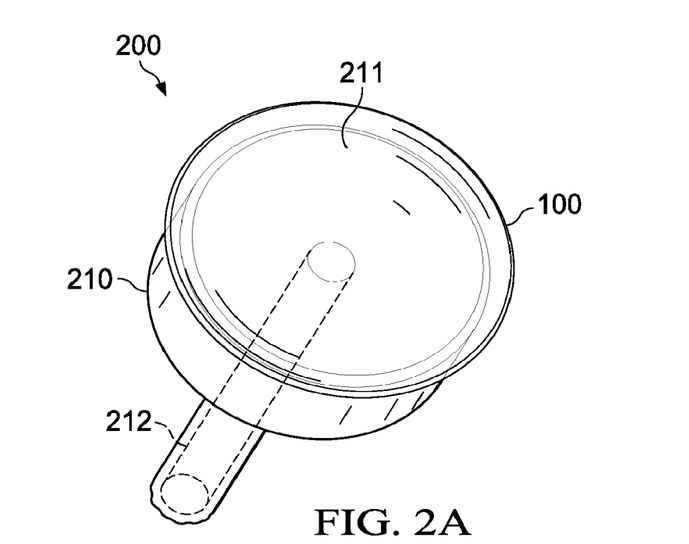
FIGS. 2A, 2B, 2C, 2D, 2E, and 2F are depictions of selected elements of different implementations of a Bernoulli gripper for IOLs and contact lenses.

Referring now to FIG. 2A, a depiction of a Bernoulli gripper 200 is shown. Bernoulli gripper 200 is shown holding contact lens 100 in a gripping position. Although Bernoulli gripper 200 is shown and referred to below holding contact lens 100 for descriptive clarity, Bernoulli gripper 200 may be enabled to grip and release various different kinds of lenses, as described herein. Bernoulli gripper 200 is comprised of a gripper body 210 having a gripper cavity 211 formed therein. Gripper cavity 211 may have different shapes in different implementations for gripping particular lenses or particular types of lenses. For example, in other implementations, gripper cavity 211 may have different shapes, and may be a protrusion instead of a cavity, such as a convex protrusion (not shown), for gripping various kinds of lenses, such as for gripping contact lens 100 on a concave surface. Bernoulli gripper 200 also includes a fluid line 212 that is fluidically coupled to gripper cavity 211 and penetrates the gripper cavity 211. Fluid line 212 may be supplied with a fluid medium, such as flowing air, at a port formed into gripper body 210 that receives a corresponding receptacle, for example.

Bernoulli gripper 200 and other Bernoulli grippers disclosed herein may operate using the Bernoulli effect, which is based on the fact that a high velocity fluid stream has a low static pressure. With a careful design, the pressure in the high velocity fluid stream can be lower than atmospheric pressure. When an object is placed against the high velocity fluid stream, the difference in pressure between atmospheric pressure on one side of the object and the lowered pressure from the high velocity fluid stream on the other side of the object can create a net pressure force that acts on the object in a direction towards the high velocity fluid stream, which is known as the Bernoulli effect.

A Bernoulli gripper takes advantage of the Bernoulli effect by maintaining a lowered pressure at the gripper face compared to the ambient pressure, while maintaining an air gap between the gripper face and the object being held. In this manner, a lens may be held, stored, and handled without any physical contact or merely with sporadic or incidental contact. To maintain the lowered pressure, the lens is subject to the one-sided flow of a fluid medium (e.g., air) through the Bernoulli gripper, specifically using a fluid line. The gripper is placed in close proximity to the lens (e.g. by positioning the gripper body) and is correspondingly contoured to the shape of the lens on the flow side. The fluid medium flows through the fluid line and exits the gripper face with high velocity, along a path between the flow-side surface of the lens and the surface of the gripper face. In contrast, on the exterior side of the lens not facing the gripper, no discernable medium flow occurs and atmospheric pressure is observed. On the flow-side surface of the lens, a pressure drop is created according to the Bernoulli effect. Through the atmospheric pressure acting on the exterior side of the lens, a net pressure force acts on the lens in the direction of the flowing fluid, which holds the lens in place against the gripper face and results in gripping of the lens in a contact-free manner.

In operation of Bernoulli gripper 200, gripper cavity 211 (i.e., the gripper face) formed in gripper body 210 holds contact lens 100 in place while pressurized air is supplied through fluid line 212 in a direction towards gripper cavity 211 to generate the pressure force for gripping contact lens 100. When the flow of pressurized air through fluid line 212, which penetrates gripper body 210 at gripper cavity 211, is discontinued, the pressure force against contact lens 100 is removed, and contact lens 100 is released and is no longer held in place in gripper cavity 211. Thus, by switching the pressurized air flow on and off, gripping and release control of Bernoulli gripper 200 may be achieved. In operation, Bernoulli gripper 200 may be implemented in a special rig, such as a pick-and-place robot, that can align or precisely position contact lens 100, including rotational, lateral, azimuthal, and axial alignment or positioning, by correspondingly moving Bernoulli gripper 200 when gripping contact lens 100.

Figure 2B:
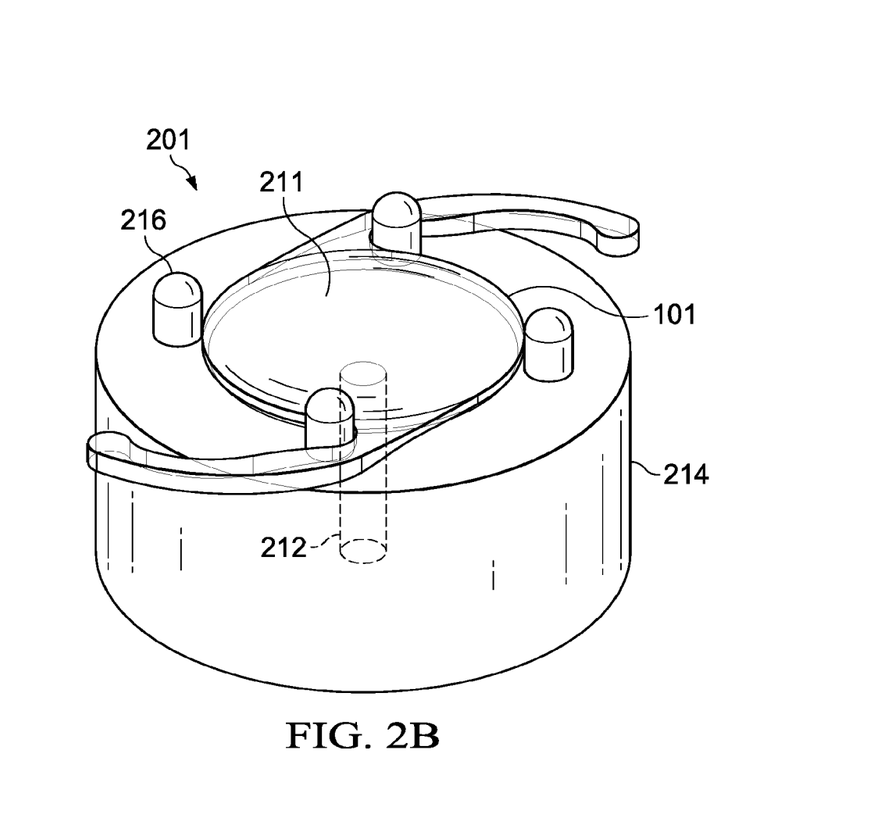

In FIG. 2B, a depiction of a Bernoulli gripper 201 is shown. Bernoulli gripper 201 is shown holding IOL 101 in a gripping position. Although Bernoulli gripper 201 is shown and referred to below holding IOL 101 for descriptive clarity, Bernoulli gripper 201 may be enabled to grip and release various different kinds of lenses, as described herein. Bernoulli gripper 201 is comprised of a gripper body 214 having a gripper cavity 211 formed therein, which may operate in substantially the same manner as described above for Bernoulli gripper 200 in FIG. 2A. Additionally, Bernoulli gripper 201 is shown including mechanical stops 216, which are mechanical protrusions in gripper body 214 at gripper cavity 211 or adjacent to gripper cavity 211. Mechanical stops 216 may provide mechanical detention for haptics 112 in order to prevent or control rotation of IOL 101 when gripped by Bernoulli gripper 201. In some implementations, mechanical stops 216 may further prevent radial slippage of IOL 101, and so, may maintain lateral alignment of IOL 101 in gripper cavity 211. For example, when IOL 101 does not include haptics, IOL 101 may rotate while maintaining a lateral alignment due to mechanical stops 216. The incidental contact between mechanical stops 216 and edges of haptics 112 may be acceptable for various industrial operations and may not adversely affect IOL 201 when gripped by Bernoulli gripper 201. Accordingly, mechanical stops 216 may be dimensioned in length to correspond to a thickness of haptics 112, for example. Although 4 (four) mechanical stops 216 are shown in FIG. 2B, it will be understood that fewer or more mechanical stops may be implemented in various designs of Bernoulli gripper 201.

Figure 2C:
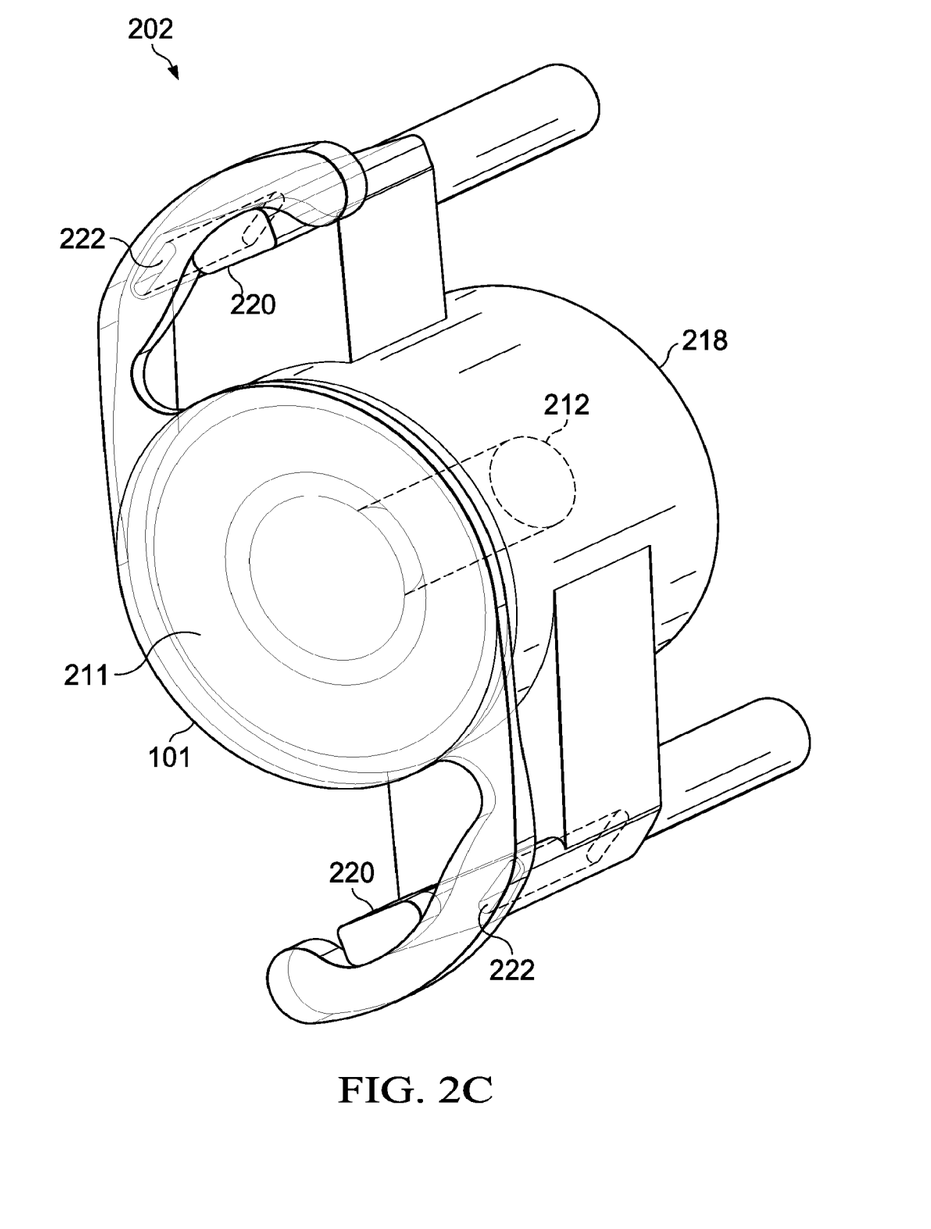

In FIG. 2C, a depiction of a Bernoulli gripper 202 is shown. Bernoulli gripper 202 is shown holding IOL 101 in a gripping position. Although Bernoulli gripper 202 is shown and referred to below holding IOL 101 for descriptive clarity, Bernoulli gripper 202 may be enabled to grip and release various different kinds of lenses, as described herein, and in particular, various different kinds of IOLs 101 with different kinds of haptics 112. Bernoulli gripper 202 is comprised of a gripper body 218 having a gripper cavity 211 formed therein, which may operate in substantially the same manner as described above for Bernoulli gripper 200 in FIG. 2A. Additionally, Bernoulli gripper 202 is shown including two mechanical stops 220, which are formed as two arms that protrude from gripper body 218 and correspond to haptics 112 of IOL 101. Specifically, the shape and position of mechanical stops 220 may be particularly designed to mate with the shape and length of haptics 112. In operation, as IOL 101 is gripped by Bernoulli gripper 202, haptics 112 on either side of IOL 101 will respectively engage with mechanical stops 220 and will rotationally immobilize IOL 101 in a specific position, as shown in FIG. 2C.

Additionally, Bernoulli gripper 202 is shown including a vacuum port 222 at each mechanical stop 220. Each of vacuum ports 222 may be supplied with underpressure or vacuum through a corresponding fluid line that is independent of fluid line 212. Thus, as shown, Bernoulli gripper 202 may use one pressurized fluid line for gripping, and two vacuum lines for fixing haptics 112 at mechanical stops 220. Fluid line 212 and vacuum lines for vacuum ports 222 may be supplied at respective ports formed into gripper body 218 that receive a corresponding receptacle, for example. In operation, as IOL 101 is gripped by Bernoulli gripper 202 and haptics 112 on either side of IOL 101 respectively engage with mechanical stops 220, a vacuum or underpressure may be switched on at vacuum ports 222 in order to provide an adhesion force that holds haptics 112 fixed at mechanical stops 220. Thus, vacuum ports 222 may be used to increase stability and positional precision involved with positioning IOL 101 using Bernoulli gripper 202, because mechanical stops 220 and vacuum ports 222 may prevent IOL 101 from rotating when gripped and may hold IOL 101 in a fixed and defined position. The incidental contact between mechanical stops 222 and faces of haptics 112 may be acceptable for various industrial operations and may not adversely affect IOL 101 when gripped by Bernoulli gripper 202. Although haptics 112 may come into contact with mechanical stops 220, the remaining portions of IOL 101, including optic zone 110, may remain without physical contact to gripper body 218. It is noted that in some implementations, mechanical stops 220 may be used without vacuum ports 222.

Figure 2D:
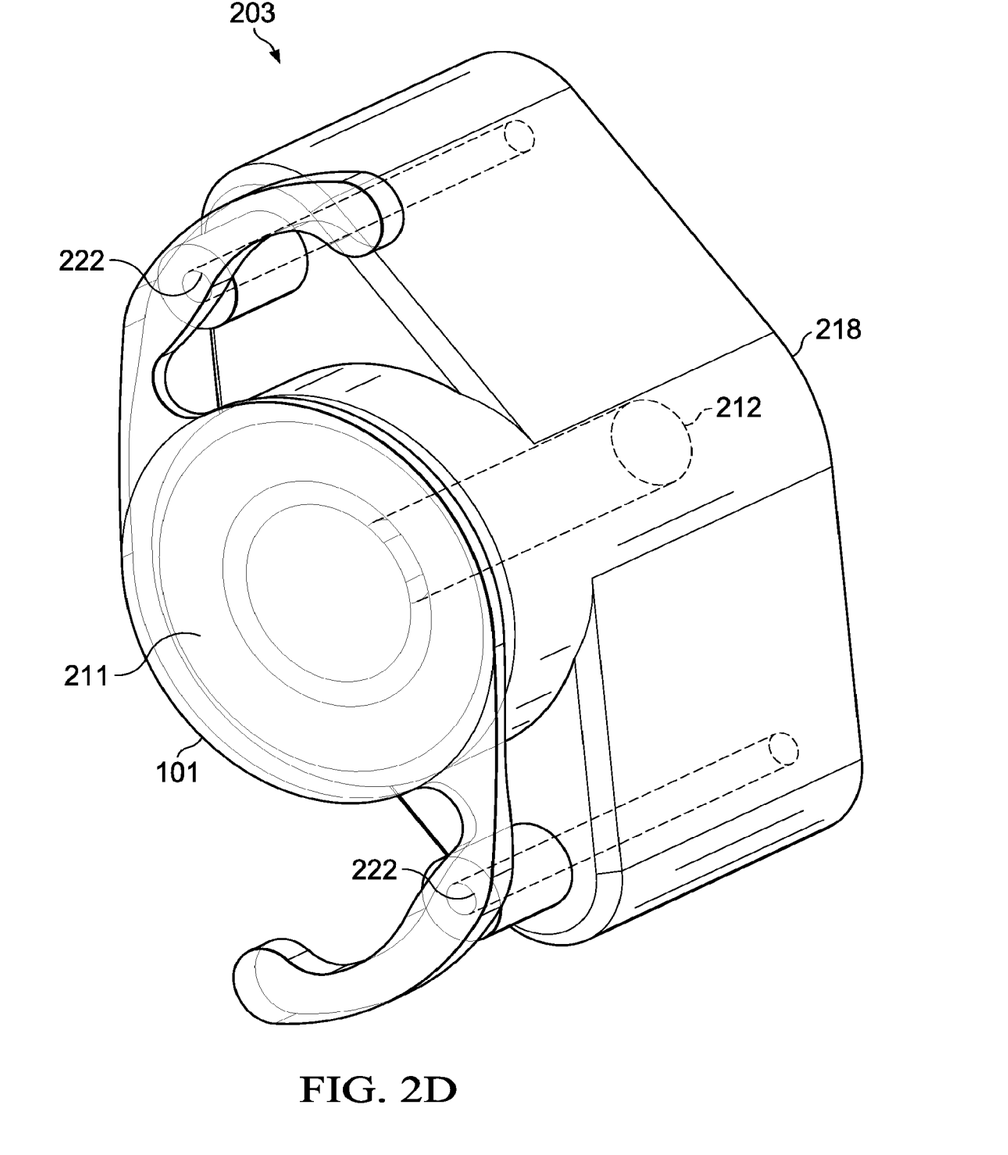

In FIG. 2D, a depiction of a Bernoulli gripper 203 is shown. Bernoulli gripper 203 is shown holding IOL 101 in a gripping position. Although Bernoulli gripper 203 is shown and referred to below holding IOL 101 for descriptive clarity, Bernoulli gripper 203 may be enabled to grip and release various different kinds of lenses, as described herein, and in particular, various different kinds of IOLs 101 with different kinds of haptics 112. Bernoulli gripper 203 is comprised of a gripper body 218 having a gripper cavity 211 formed therein, which may operate in substantially the same manner as described above for Bernoulli gripper 200 in FIG. 2A. Additionally, Bernoulli gripper 203 is shown including two vacuum ports 222 at each side portion of gripper body 218, corresponding to a location of haptics 112. Each of vacuum ports 222 may be supplied with underpressure or vacuum through a corresponding fluid line that is independent of fluid line 212. Thus, as shown, Bernoulli gripper 203 may use one pressurized fluid line for gripping, and two vacuum lines for fixing haptics 112 at vacuum ports 222. Fluid line 212 and vacuum lines for vacuum ports 222 may be supplied at respective ports formed into gripper body 218 that receive a corresponding receptacle, for example. In operation, as IOL 101 is gripped by Bernoulli gripper 203, haptics 112 on either side of IOL 101 are subject to a vacuum or underpressure that may be switched on at vacuum ports 222 in order to provide an adhesion force that holds haptics 112 fixed at vacuum ports 222. Thus, vacuum ports 222 may be used to increase stability and positional precision involved with positioning IOL 101 using Bernoulli gripper 203, because vacuum ports 222 may prevent IOL 101 from rotating when gripped and may hold IOL 101 in a fixed and defined position. The incidental contact between vacuum ports 222 and faces of haptics 112 may be acceptable for various industrial operations and may not adversely affect IOL 101 when gripped by Bernoulli gripper 203. Although haptics 112 may come into contact with vacuum ports 222, the remaining portions of IOL 101, including optic zone 110, may remain without physical contact to gripper body 218.

Figure 2E:
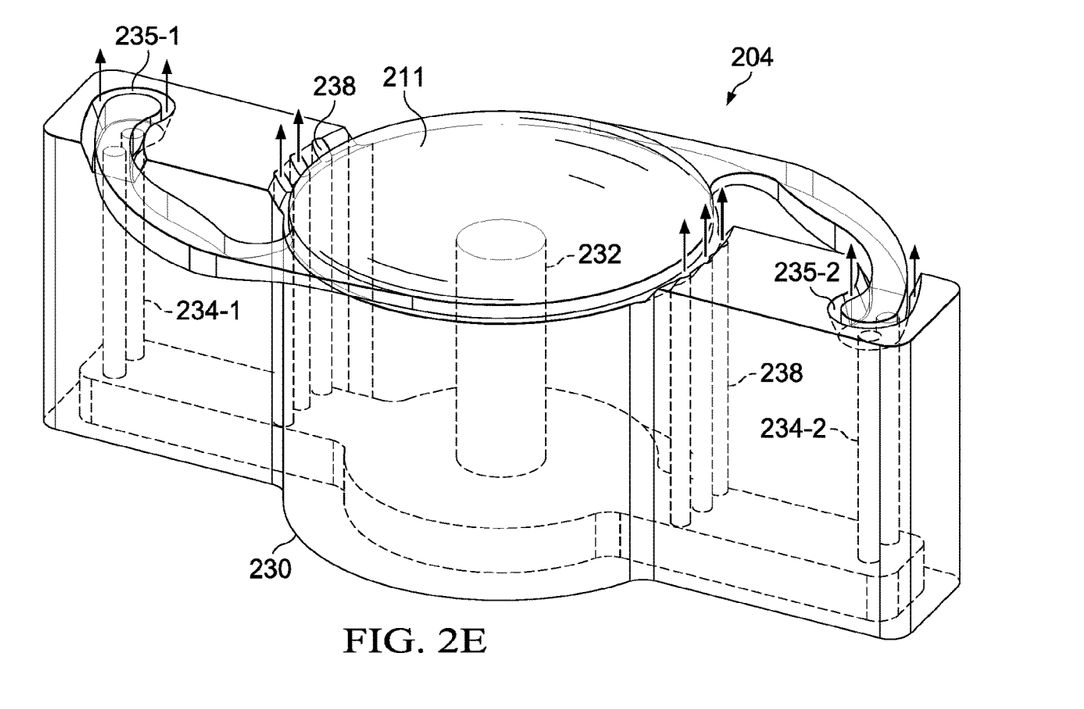
Figure 2F:
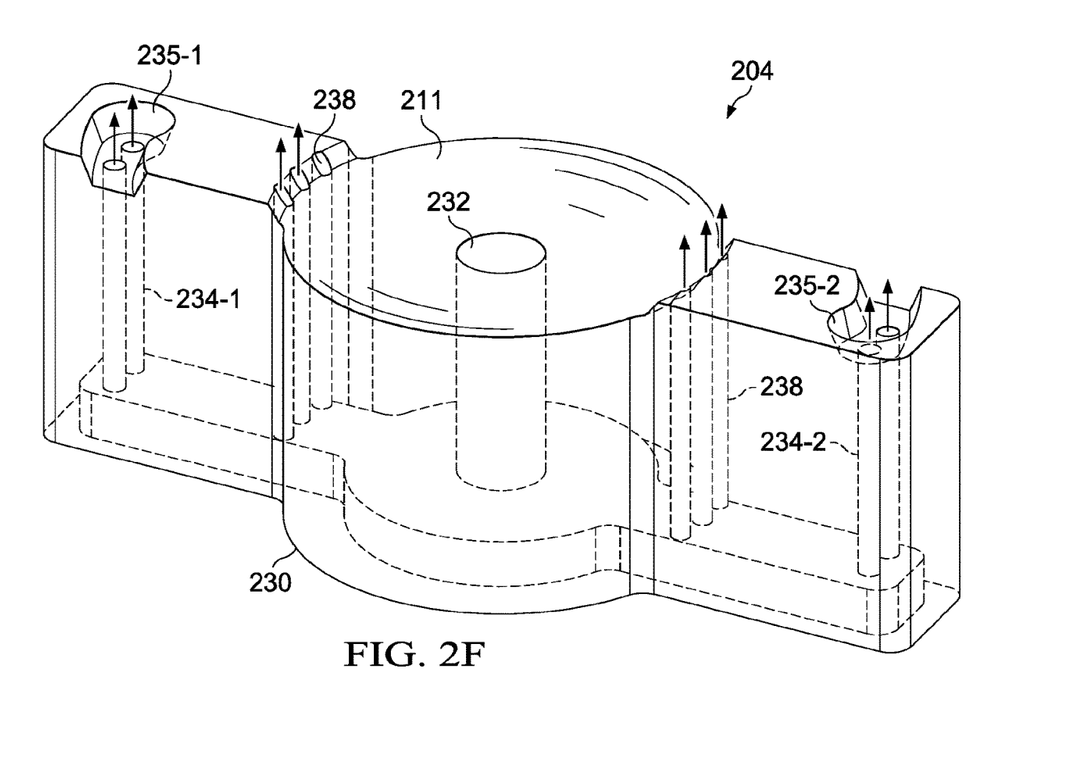

In FIGS. 2E and 2F, a depiction of a Bernoulli gripper 204 is shown. Bernoulli gripper 204 is shown in two views: without an IOL (FIG. 2F) and holding IOL 101 in a gripping position (FIG. 2E). Although Bernoulli gripper 204 is shown and referred to below holding IOL 101 for descriptive clarity, Bernoulli gripper 204 may be enabled to grip and release various different kinds of lenses, as described herein, and in particular, various different kinds of IOLs 101 with different kinds of haptics 112. Bernoulli gripper 204 is comprised of a gripper body 230 having a main gripper cavity 211 and two haptic cavities 235-1 and 235-2 formed therein, which may operate in substantially the same manner as described above for Bernoulli gripper 200 in FIG. 2A.

In Bernoulli gripper 204, main gripper cavity 211 may accordingly be used to grip IOL 101 at optic zone 110 using the Bernoulli effect, as described previously, in which a fluid medium (e.g. air) is supplied by fluid line 232 to a central opening that penetrates main gripper cavity 211. Thus, main gripper cavity 211 and fluid line 232 are operable to provide a first pressure force on IOL 101 that is normal to main gripper cavity 211. Additionally, main gripper cavity 211 may be equipped with additional fluid lines 238 that are formed at peripheral edges of main gripper cavity 211 at a location that corresponds to lateral edges of IOL 101 when IOL 101 is gripped by gripper body 230. Additional fluid lines 238 may be used to supply additional flows of the fluid medium that impart lateral pressure forces to IOL 101 in order to facilitate centering or alignment of IOL 101 within main gripper cavity 211. Specifically, as the fluid medium leaves a peripheral port of fluid line 238, a pressure drop is created between the lateral edge of IOL 101 and the lateral edge of main gripper cavity 211, causing IOL 101 to be laterally forced against the lateral edge of main gripper cavity 211. As fluid lines 238 on different sides of main gripper cavity 211 are subject to the flow of the fluid medium, the lateral forces will counteract each other and will serve to maintain IOL 101 in a central position when the respective flow rates in fluid lines 238 are adjusted for symmetrical operation. In this manner, IOL 101 may be prevented from contacting main gripper cavity 211 at the lateral edges of IOL 101.

Furthermore, in Bernoulli gripper 204, haptic cavities 235-1 and 235-2 may respectively receive distal portions of haptics 112 of IOL 101. Haptic cavities 235-1 and 235-2 may accordingly be shaped and dimensioned to correspond to the distal portions of haptics 112. Haptic cavities 235-1 and 235-2 may also be equipped with haptic fluid lines 234 in order to provide Bernoulli gripping of the distal portions of haptics 112. For example, each haptic cavity 235 may include one or more fluid lines 234 that are independent of fluid line 232. Haptic fluid lines 234-1 and 234-2 may operate in a similar manner on haptics 112 as fluid line 232 operates with respect to optic zone 110, by using the Bernoulli effect to generate a pressure force at haptic 112 that is normal to gripper body 230 and that holds each respective haptic 112 in place within haptic cavity 235-1 and 235-2, as shown in FIG. 2E. Fluid lines 232, 234-1, 234-2, and 238 may be supplied at respective ports formed into gripper body 230 that receive a corresponding receptacle, for example. It is noted that flow rates for the fluid medium in fluid lines 232, 234-1, 234-2, and 238 may be independently controlled and operated, and may correspondingly be used to provide different levels of pressure forces, as desired.

As shown in the above examples of Bernoulli grippers, various different kinds of ophthalmic lenses, such as various IOLs and contact lenses, among others, can be gripped in a substantially contact-free manner. The gripping and holding of contact lenses or IOLs is generally a technical challenge, because such lenses have a very sensitive surface that can render the lens unusable when damaged. With contact-free gripping using the Bernoulli grippers disclosed herein, damage to the surface of the lens can be avoided. The gripping using the Bernoulli grippers disclosed herein may be performed for positioning, transporting, or storing or holding lenses fixed for an industrial process. The Bernoulli grippers disclosed herein may be advantageously used when lenses have a sticky or adhesive surface and are surface sensitive to contact during the manufacturing process, in order to guide a lens from one process station to another and precisely put the lens down and release the lens without damage, such as a pick-and-place process operation that repeats every 5 to 10 seconds or longer, for example.

The Bernoulli grippers disclosed herein may also enable holding lenses in a medium during an extraction or a coating process without obscuring or masking a surface portion of the lens. Concurrently, the lenses may be washed by the medium without any localized masking, which is advantageous for the exchange of molecules between the medium and the lens, such as for cleaning, drying, or degassing operations performed in a substantially contact-free manner, for example. Specifically, during the manufacture of IOLs, surface damage may occur when a contacting carrier is used to hold the IOL. The Bernoulli grippers disclosed herein can be advantageously used to enable drying contact lenses and IOLs in a substantially contact-free manner to avoid any issues with potential surface damage from undesired contact with the carrier. On the one hand, the contact-free drying enabled by the Bernoulli grippers disclosed herein prevents sticking and damaging of the lenses. In addition, a more homogenous drying operation is possible with the Bernoulli grippers disclosed herein because the lens is freely exposed to air, in contrast to gripping the lens using a contacting gripper.

In addition, the appearance of static charge can make the gripping and placing of lenses using conventional vacuum grippers difficult, such as by the manufacture of contact lenses with double sided molding (DSM) process. Here the attractive static forces can be very large due to the minimal gap with the gripper and can lead in subsequent placement processes to sticking of the lens. The Bernoulli grippers disclosed herein may also be used to hold electrostatically charged lenses that are difficult or impossible to release from a conventional gripper due to the charged condition of the lens. For example, with the use of ionized air as the fluid medium in the Bernoulli gripper, the lens surface can be simultaneously ionically discharged for further process steps. With the use of the Bernoulli gripper disclosed herein, the direct contact between the gripper and the lens is prevented on the one hand, by which the induced electrostatic forces are kept relatively small, and on the other hand, the lens can be neutralized using ionized air and made easier to handle for further process steps. Through the use of ionized air as the fluid medium, the lens surface can be electrostatically neutralized, which improves further handling, and the accumulation of dirt particles is reduced, which may be particularly advantageous for optical lenses.

A further special example for the advantageous use of the Bernoulli gripper disclosed herein is the drying process during manufacture of IOLs. After extraction, the IOLs have a very sticky surface that may be statically charged, and are also swollen from the absorbed extraction medium. During drying of the IOL, contact-free gripping of the IOL using the Bernoulli gripper disclosed herein may allow the IOL to shrink without contact or adhesion to the gripper surface, which is desirable to prevent damage to and to protect the IOL.

Figure 3:
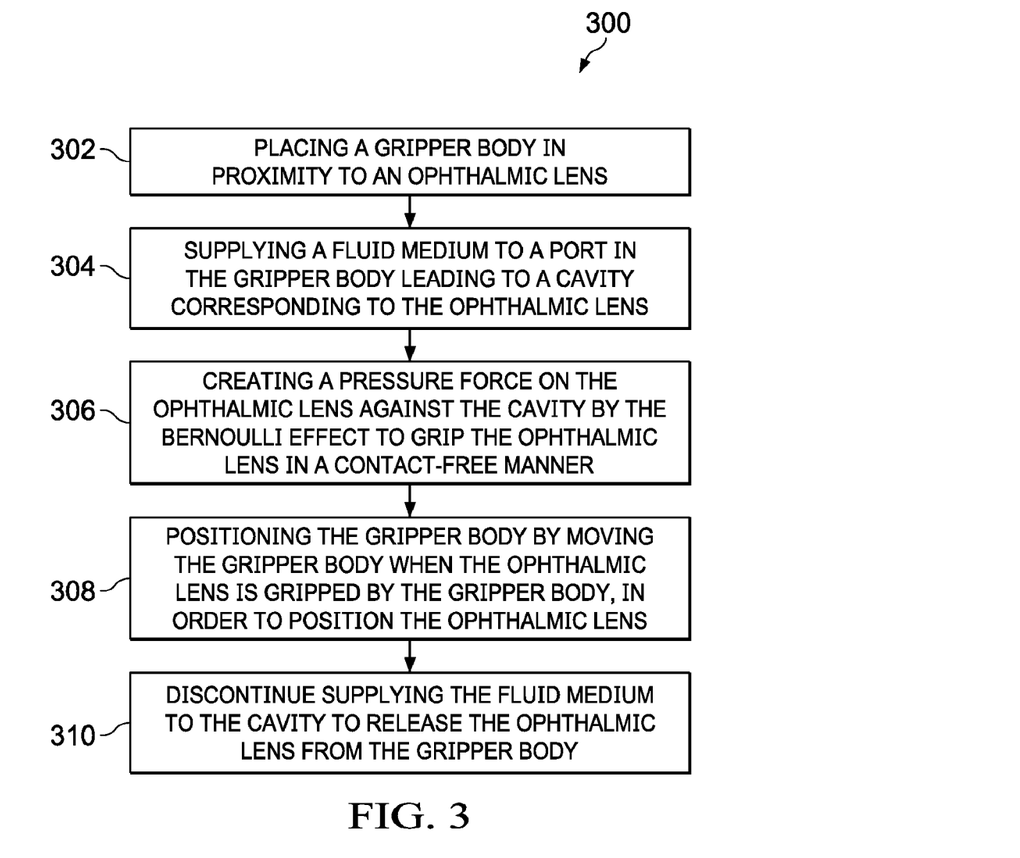
FIG. 3 is a flow chart of selected elements of a method for operating a Bernoulli gripper with an ophthalmic lens.

Referring now to FIG. 3, a flow chart of selected elements of an embodiment of a method 300 for operating a Bernoulli gripper with an ophthalmic lens, as disclosed herein. It is noted that certain operations described in method 300 may be optional or may be rearranged in different embodiments. Method 300 may be performed using any of the Bernoulli grippers disclosed herein.

Method 300 may begin, at step 302, by placing a gripper body in proximity to an ophthalmic lens. The ophthalmic lens may be an IOL or a contact lens, among others. The gripper body may be placed within a proximity of until less than a mm to the ophthalmic lens. At step 304, a fluid medium is supplied to a port in the gripper body leading to a cavity corresponding to the ophthalmic lens. As noted above, the gripper body may have a cavity that is formed to correspond to the surface of the ophthalmic lens being gripped, which may be a concave cavity. In other cases, gripper body may have a convex protrusion instead of a concave cavity. The fluid medium may be air or ionized air or another gas, for example. At step 306, a pressure force is created on the ophthalmic lens against the cavity by the Bernoulli effect to grip the ophthalmic lens in a contact-free manner. Because the pressure force pushes the ophthalmic lens against the flowing fluid medium, the ophthalmic lens remains free of physical contact to the cavity and the gripper body. At step 308, the gripper body is positioned by moving the gripper body when the ophthalmic lens is gripped by the gripper body, in order to position the ophthalmic lens. The positioning and moving in step 308 may include translation or rotation or any combination thereof. At step 310, supplying the fluid medium to the cavity is discontinued to release the ophthalmic lens from the gripper body.

As disclosed herein, a Bernoulli gripper is specially designed to isolate and transport ophthalmic lenses, such as IOLs and contact lenses, in a substantially contact-free manner.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A Bernoulli gripper for ophthalmic lenses, the Bernoulli gripper comprising:
a gripper body with a first cavity corresponding in shape to an optic zone of an ophthalmic lens;
a first channel formed within the gripper body, the first channel penetrating the first cavity at a first end of the first channel; and
a second channel formed within the gripper body, the second channel penetrating the gripper body at a first end of the second channel, wherein:
the first channel is enabled to subject the ophthalmic lens, positioned with the optic zone in proximity to the first cavity, to a first pressure force against the first cavity by a Bernoulli effect, and
the second channel is enabled to subject at least a portion of the ophthalmic lens positioned in proximity to the second channel to a second pressure force different from the first pressure force.

2. The Bernoulli gripper of claim 1, wherein the first pressure force is sufficient to grip the ophthalmic lens at the first cavity to enable positioning of the ophthalmic lens when the gripper body is correspondingly positioned.

3. The Bernoulli gripper of claim 1, wherein the first cavity is enabled to grip the ophthalmic lens without the optic zone contacting the first cavity when the first pressure force acts against the first cavity.

4. The Bernoulli gripper of claim 1, wherein the first channel is enabled to supply an electrostatically charged fluid medium.

5. The Bernoulli gripper of claim 1, wherein the first channel is enabled to supply air.

6. The Bernoulli gripper of claim 1, wherein the ophthalmic lens is an intraocular lens comprising the optic zone and a haptic, and further comprising a mechanical stop to detain the haptic and prevent rotation of the ophthalmic lens, wherein the at least the portion of the ophthalmic lens comprises the haptic.

7. The Bernoulli gripper of claim 6, wherein the mechanical stop further comprises a second cavity correspondingly formed to receive a distal portion of the haptic, wherein the second channel penetrates the second cavity at the first end of the second channel, wherein the second channel is enabled to supply a fluid medium to the second cavity at a velocity such that the haptic positioned in proximity to the second cavity is subject to the second pressure force against the second cavity by the Bernoulli effect.

8. The Bernoulli gripper of claim 6, wherein:
the second channel penetrates the mechanical stop at the first end of the second channel,
the second pressure force is applied to the haptic when the haptic is detained by the mechanical stop, and
the second pressure force comprises underpressure.

9. The Bernoulli gripper of claim 1, wherein:
the first channel penetrates the first cavity at a center portion of the first cavity, and
the second channel penetrates an edge portion of the first cavity at the first end of the second channel,
wherein the second channel is enabled to supply a fluid medium to the edge portion of the first cavity at a velocity such that the ophthalmic lens, positioned with the optic zone in proximity to the first cavity, is subject to the second pressure force laterally within the first cavity by the Bernoulli effect.

10. The Bernoulli gripper of claim 1, wherein:
the ophthalmic lens is an intraocular lens comprising the optic zone and a haptic,
the second pressure force is applied to the haptic when the optic zone is detained in the first cavity, and
the second pressure force comprises underpressure.

11. A Bernoulli gripper for intraocular lenses, the Bernoulli gripper comprising:
a gripper body with a cavity corresponding in shape to an optic zone of an intraocular lens;
a first channel formed within the gripper body, the first channel penetrating the cavity at a first end of the first channel;
a mechanical stop enabled to detain a haptic of the intraocular lens to prevent rotation of the intraocular lens; and
a second channel formed within the gripper body, the second channel penetrating the gripper body at a first end of the second channel and penetrating the mechanical stop at second end of the second channel;

wherein:
the first channel is enabled to supply a first fluid medium to the cavity at a first velocity such that the intraocular lens positioned with the optic zone in proximity to the cavity is subject to a first pressure force against the cavity by a Bernoulli effect; and
the second channel is enabled to subject at least a portion of the intraocular lens positioned in proximity to the second channel to a second pressure force, wherein the second pressure force is applied to the haptic when the haptic is detained by the mechanical stop, and wherein the second pressure force comprises underpressure.

12. The Bernoulli gripper of claim 11, wherein:
the mechanical stop protrudes from the gripper body, and
a side of the mechanical stop is enabled to engage a side of the haptic to detain the intraocular lens.

13. The Bernoulli gripper of claim 11, wherein the first pressure force is sufficient to grip the intraocular lens at the cavity to enable positioning of the intraocular lens when the gripper body is correspondingly positioned.

14. The Bernoulli gripper of claim 11, wherein the cavity is enabled to grip the intraocular lens without the optic zone contacting the cavity when the first pressure force acts against the cavity.

15. The Bernoulli gripper of claim 11, wherein the first channel is enabled to supply the first fluid medium when the first fluid medium is electrostatically charged.

16. The Bernoulli gripper of claim 11, wherein
the second channel is enabled to supply a second fluid medium to
the mechanical stop at a second velocity such that the haptic detained by the mechanical stop is subject to the second pressure force.

17. A method for gripping ophthalmic lenses, the method comprising:
placing a gripper body in proximity to an ophthalmic lens, the gripper body having:
a first cavity corresponding in shape to an optic zone of the ophthalmic lens;
a first channel formed within the gripper body, the first channel penetrating the first cavity at a first end of the first channel; and
a second channel formed within the gripper body, the second channel penetrating the gripper body at a first end of the second channel;
subjecting the ophthalmic lens positioned with the optic zone in proximity to the first cavity to a first pressure force against the first cavity by a Bernoulli effect through the first channel; and
subjecting at least a portion of the ophthalmic lens positioned in proximity to the second channel to a second pressure force different from the first pressure force through the second channel.

* * * * *